(12) United States Patent
Whittaker et al.

(10) Patent No.: US 9,226,759 B2
(45) Date of Patent: Jan. 5, 2016

(54) LOW PROFILE REAMERS AND METHODS OF USE

(71) Applicant: DePuy Mitek, LLC, New Brunswick, NJ (US)

(72) Inventors: Gregory R. Whittaker, Stoneham, MA (US); Mehmet Z. Sengun, Canton, MA (US); Kristian Dimatteo, Waltham, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 14/639,474

(22) Filed: Mar. 5, 2015

(65) Prior Publication Data

US 2015/0173778 A1    Jun. 25, 2015

Related U.S. Application Data

(62) Division of application No. 13/623,366, filed on Sep. 20, 2012, now Pat. No. 9,011,443.

(51) Int. Cl.
*A61B 17/16* (2006.01)

(52) U.S. Cl.
CPC ......... *A61B 17/1675* (2013.01); *A61B 17/1617* (2013.01)

(58) Field of Classification Search
CPC ............... A61B 17/16; A61B 17/1613; A61B 17/1615; A61B 17/1617; A61B 17/162; A61B 17/1662; A61B 17/1675
USPC ........ 606/79–81, 86 R, 96–98; 408/199, 226, 408/227
See application file for complete search history.

(56) References Cited

U.S. PATENT DOCUMENTS

| | | | | |
|---|---|---|---|---|
| 164,953 | A | * | 6/1875 | Willig ............................ 408/180 |
| 1,042,597 | A | * | 10/1912 | Pease ............................ 408/226 |
| 3,216,414 | A | * | 11/1965 | Street ............................ 606/68 |
| 3,702,611 | A | | 11/1972 | Fishbein |
| 3,719,186 | A | * | 3/1973 | Merig, Jr. ....................... 606/80 |
| 4,090,808 | A | * | 5/1978 | Nannen ......................... 408/222 |
| 4,316,683 | A | * | 2/1982 | Schott ........................... 408/219 |
| 4,711,234 | A | * | 12/1987 | Vives et al. ..................... 606/60 |
| 4,751,922 | A | * | 6/1988 | DiPietropolo ................... 606/80 |
| 5,061,113 | A | * | 10/1991 | Vives ......................... 403/408.1 |
| 5,122,134 | A | * | 6/1992 | Borzone et al. ................. 606/80 |
| 5,190,548 | A | * | 3/1993 | Davis ............................ 606/80 |
| 5,222,956 | A | * | 6/1993 | Waldron ........................ 606/80 |

(Continued)

FOREIGN PATENT DOCUMENTS

DE         3008008    *    4/1983

*Primary Examiner* — Christian Sevilla
*Assistant Examiner* — Eric S Gibson

(57) ABSTRACT

Low profile reamers and methods of use are provided which can, in general, allow a hole to be drilled in bone. In one embodiment, a low profile retractable bone reamer is provided having an elongate shaft with a cutting element disposed on a distal end of the elongate shaft that can be configured to drill a hole in bone. The elongate shaft and cutting element can have first and second longitudinally separated portions that are movably coupled to each other. The reamer can be configured to move between a retracted configuration, in which a the reamer has a reduced, low profile configuration, and a non-retracted configuration, in which both longitudinally separated portions of the cutting element can be positioned adjacent to one another to form a single cutting element.

5 Claims, 11 Drawing Sheets

(56) References Cited

U.S. PATENT DOCUMENTS

| | | | |
|---|---|---|---|
| 5,292,322 A * | 3/1994 | Faccioli et al. | 606/59 |
| 5,330,480 A * | 7/1994 | Meloul et al. | 606/80 |
| 5,374,269 A * | 12/1994 | Rosenberg | 606/80 |
| 5,405,348 A * | 4/1995 | Anspach et al. | 606/80 |
| 5,499,984 A * | 3/1996 | Steiner et al. | 606/80 |
| 5,562,673 A * | 10/1996 | Koblish et al. | 606/80 |
| 5,720,748 A * | 2/1998 | Kuslich et al. | 606/80 |
| 5,720,749 A * | 2/1998 | Rupp | 606/79 |
| 5,788,699 A * | 8/1998 | Bobst et al. | 606/80 |
| 5,855,581 A | 1/1999 | Koblish et al. | |
| 5,908,423 A * | 6/1999 | Kashuba et al. | 606/80 |
| 5,928,241 A * | 7/1999 | Menut et al. | 606/80 |
| 5,941,883 A * | 8/1999 | Sklar | 606/88 |
| 5,947,971 A | 9/1999 | Kuslich et al. | |
| 5,968,048 A * | 10/1999 | Harder | 606/80 |
| 5,980,525 A * | 11/1999 | Bryant et al. | 606/80 |
| 6,015,411 A * | 1/2000 | Ohkoshi et al. | 606/80 |
| 6,053,922 A * | 4/2000 | Krause et al. | 606/80 |
| 6,258,093 B1 * | 7/2001 | Edwards et al. | 606/80 |
| 6,270,501 B1 * | 8/2001 | Freiberg et al. | 606/79 |
| RE37,358 E * | 9/2001 | Del Rio et al. | 606/80 |
| 6,283,971 B1 | 9/2001 | Temeles | |
| 6,431,801 B2 * | 8/2002 | Vasudeva et al. | 408/211 |
| 7,011,662 B2 | 3/2006 | Lechot et al. | |
| 7,090,677 B2 | 8/2006 | Fallin et al. | |
| 7,097,646 B2 | 8/2006 | Schantz | |
| 7,608,076 B2 | 10/2009 | Ezzedine | |
| 7,632,276 B2 | 12/2009 | Fishbein | |
| 7,722,615 B2 | 5/2010 | Botimer | |
| 7,862,567 B2 * | 1/2011 | Schmieding | 606/80 |
| 7,935,117 B2 | 5/2011 | Sackett et al. | |
| 8,002,775 B2 * | 8/2011 | McKay | 606/80 |
| RE42,757 E | 9/2011 | Kuslich et al. | |
| 8,025,662 B2 | 9/2011 | Knisely et al. | |
| 8,029,509 B2 * | 10/2011 | Ducharme | 606/80 |
| 8,083,803 B2 | 12/2011 | Albertorio et al. | |
| 8,460,298 B2 * | 6/2013 | O'Donoghue | 606/80 |
| 8,709,013 B2 | 4/2014 | Lombardo | |
| 2002/0151902 A1 * | 10/2002 | Riedel et al. | 606/80 |
| 2002/0165549 A1 * | 11/2002 | Owusu-Akyaw et al. | 606/80 |
| 2003/0055431 A1 * | 3/2003 | Brannon | 606/80 |
| 2003/0130663 A1 * | 7/2003 | Walen | 606/80 |
| 2004/0093001 A1 * | 5/2004 | Hamada | 606/190 |
| 2004/0230211 A1 * | 11/2004 | Moutafis et al. | 606/167 |
| 2005/0113836 A1 | 5/2005 | Lozier et al. | |
| 2005/0283160 A1 * | 12/2005 | Knisely et al. | 606/80 |
| 2006/0100631 A1 * | 5/2006 | Sullivan et al. | 606/80 |
| 2006/0241629 A1 | 10/2006 | Krebs et al. | |
| 2007/0021752 A1 * | 1/2007 | Rogers | 606/80 |
| 2007/0276392 A1 * | 11/2007 | Beyar et al. | 606/80 |
| 2008/0140078 A1 * | 6/2008 | Nelson et al. | 606/80 |
| 2008/0306483 A1 * | 12/2008 | Iannarone | 606/83 |
| 2009/0024130 A1 * | 1/2009 | Lombardo | 606/80 |
| 2009/0138015 A1 * | 5/2009 | Conner et al. | 606/80 |
| 2009/0275950 A1 | 11/2009 | Sterrett et al. | |
| 2010/0135739 A1 * | 6/2010 | Nomura et al. | 408/59 |
| 2010/0204700 A1 * | 8/2010 | Falahee | 606/80 |
| 2010/0286694 A1 * | 11/2010 | Rio et al. | 606/80 |
| 2011/0034930 A1 * | 2/2011 | Buschmann et al. | 606/80 |
| 2012/0078256 A1 * | 3/2012 | Herdrich et al. | 606/80 |
| 2012/0203230 A1 * | 8/2012 | Adams | 606/80 |
| 2012/0259336 A1 * | 10/2012 | del Rio et al. | 606/80 |
| 2012/0259337 A1 * | 10/2012 | del Rio et al. | 606/80 |
| 2014/0081271 A1 * | 3/2014 | Whittaker et al. | 606/80 |

* cited by examiner

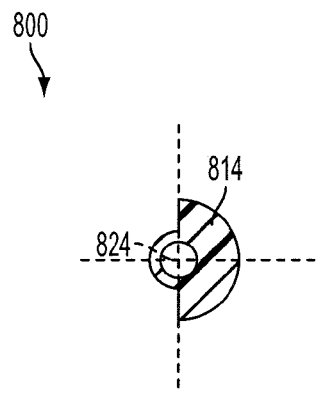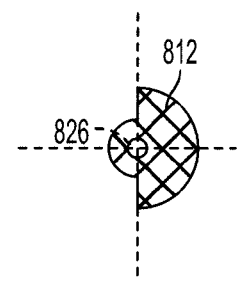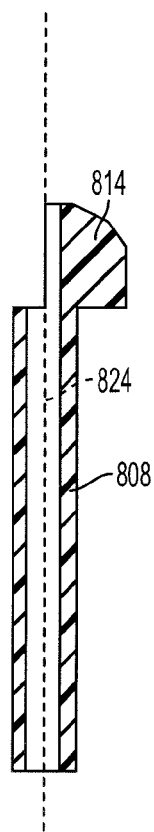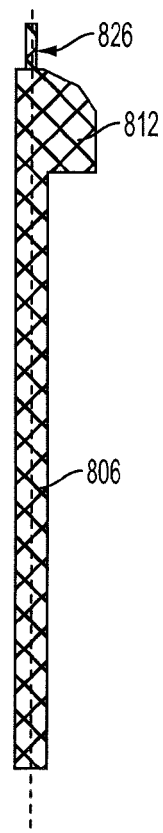
FIG. 9A
FIG. 9C
FIG. 9B
FIG. 9D

LOW PROFILE REAMERS AND METHODS OF USE

CROSS REFERENCE TO RELATED APPLICATIONS

This application is a divisional of U.S. application Ser. No. 13/623,366, filed on Sep. 20, 2012, and entitled "Low Profile Reamers and Methods of Use," which is hereby incorporated by reference in its entirety.

FIELD OF THE INVENTION

The present invention relates generally to methods and devices for creating tunnels in bone, such as bone tunnels for ligament reconstruction.

BACKGROUND

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents or overexertion. Accordingly, various procedures have been developed to repair or replace such damaged ligaments. For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the ACL is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

Two popular approaches to ACL reconstruction include a transtibial approach and an anteromedial approach. In the transtibial approach, a surgeon will first drill a tunnel through a tibia and insert a guide pin through the tunnel and through intra-articular space between a femur and the tibia to locate and drill an aligned femoral tunnel. Once the guide pin is placed, a reamer overdrills the guide pin and passes into the femur to create a final diameter of the femoral tunnel in which a ligament graft can be positioned and secured. Such an approach, however, can be difficult as the femoral tunnel entrance can be constrained by the position and trajectory of the tibial tunnel.

In the anteromedial approach, a surgeon inserts the guide pin directly into the femur through an Anterior Medial ("AM") portal, which renders initial drilling of the tibia unnecessary. By reaming a femoral tunnel through the AM portal, the femoral tunnel entrance can be located closer to where the ACL was attached to the femur and thus, can result in a more anatomical ACL reconstruction. However, due to the "shallow" angle of approach directly into the femur, the trajectory brings the guide pin much closer to articular cartilage in the intra-articular space than in the transtibial approach. Since the reamer will have a larger diameter than the guide pin, it can be challenging to place the reamer over the guide pin without scraping or damaging the articular cartilage of the medial femoral condyle because of inadequate clearance in the anteromedial approach.

Accordingly, there remains a need for improved methods and devices for creating tunnels in bone.

SUMMARY

The present invention generally provides bone reamers and methods of use. In one embodiment, a surgical bone reamer is provided and includes a first elongate shaft having proximal and distal ends, and a second elongate shaft having proximal and distal ends. The distal end of the first elongate shaft has a first cutting element formed thereon and positioned offset from a central axis of the first elongate shaft, and the distal end of the second elongate shaft has a second cutting element formed thereon and positioned offset from a central axis of the second elongate shaft. The second elongate shaft can be moveably coupled to the first elongate shaft such that the first and second cutting elements can be positioned adjacent to one another to form a single cutting element extending substantially symmetrically about a longitudinal axis extending between the first and second elongate shafts.

While the shaft can have a variety of configurations, in one embodiment the second elongate shaft is longitudinally slidably coupled to the first elongate shaft. In another embodiment, the second elongate shaft is rotatably coupled to the first elongate shaft. In yet another embodiment, the first cutting element can be formed on a first side of the first elongate shaft, and a second opposite side of the first elongate shaft can extend linearly along an entire length thereof, and the second cutting element can be formed on a first side of the second elongate shaft, and a second opposite side of the second elongate shaft can extend linearly along an entire length thereof. The second side of the first elongate shaft can be mated to the second side of the second elongate shaft. While various mating features can be used, by way of non-limiting example the first elongate shaft can include a male mating element formed thereon and the second elongate shaft can include a female mating element formed thereon for slidably mating with the male mating element on the first elongate shaft. In other aspects, the first and second elongate shafts can be keyed together such that the shafts are fixed radially and slidable axially. In another embodiment, the surgical bone reamer can include a collar having a proximal end configured to mate to a driving element, and a distal end that is coupled to the proximal end of each of the first and second elongate shafts. In yet another embodiment, the first and second elongate shafts can include a lumen formed therebetween for receiving a guidewire The cutting elements can also have a variety of configurations. For example, when the first and second cutting elements are positioned together, the cuttings members can have a substantially bulbous shape. In another embodiment, when the first and second cutting elements are positioned together, the cutting elements can taper radially inward at a distal-most end to form a pointed tip. In other aspects, the first and second cutting elements can include a plurality of flutes formed therein for cutting bone.

In yet another embodiment, a surgical bone reamer is provided and includes an elongate shaft having a proximal end configured to mate to a driver, and a distal end. The elongate shaft can include first and second longitudinally separated portions, and the first and second portions can be moveably coupled to one another. The reamer can also include a cutting element formed on the distal end of the elongate shaft and configured to form a bore hole in bone. The cutting element can include first and second longitudinally separated portions, the first portion being formed on a distal end of the first portion of the elongate shaft, and the second portion being formed on a distal end of the second portion of the elongate shaft such that the first and second portions of the elongate shaft can move relative to one another to move the first and second portions of the cutting element relative to one another. In an exemplary embodiment, a maximum outer diameter of the cutting element is greater than a maximum outer diameter of the elongate shaft.

While the shaft can have various configurations, in one embodiment an inner wall of the first portion of the elongate shaft can include a recess and an inner wall of the second portion of the elongate shaft can include a protrusion. The recess and the protrusion can be slidably engaged to slidably couple the first and second portions of the elongate shaft. The recess can extend along a partial length or the entire length of the first portion of the elongate shaft and the first portion of the cutting element, and the protrusion can extend along a partial length or the entire length of the second portion of the elongate shaft and the second portion of the cutting element. In another embodiment, the first portion of the elongate shaft can include a plurality of recesses and the second portion of the elongate shaft can include a plurality of protrusions that slidably couple to the plurality of recesses. In another embodiment, the reamer can include an outer cannula, and the first and second portions of the elongate shaft can be slidably disposed within the outer cannula such that the outer cannula radially fixes and longitudinally slidably couples the first and second portions of the elongate shaft.

In yet another embodiment, a method for forming a bore hole in bone is provided and can include inserting a distal portion of a bone reamer through tissue to position the distal portion of the bone reamer adjacent to bone, the bone reamer can include a first portion of a shaft moveably coupled to a second portion of the shaft, a first cutting element disposed on a distal end of the first portion of the shaft, and a second cutting element disposed on a distal end of the second portion of the shaft, rotating the first portion of the shaft of the bone reamer and the first cutting element, and activating a driver coupled to the bone reamer to rotate the bone reamer and thereby cause the first and second cutting elements to form a bore hole in the bone. In some embodiments, after rotating and prior to activating, a user can slidably advance one of the first portion of the shaft and the second portion of the shaft to thereby position the first and second cutting elements adjacent to one another. And in yet another embodiment, rotating the first portion of the shaft of the bone reamer rotates the second cutting element such that the second cutting element is positioned away from a medial condyle. The bone can be, for example, a tibia or femur. The first and second cutting elements can be positioned adjacent to one another when the bone reamer is inserted through tissue, or they can be spaced longitudinally. In other aspects, inserting the bone reamer through tissue can include positioning a distal end of the bone reamer adjacent to a medial condyle of a femur. In another embodiment, the bone reamer can be advanced over a guidewire.

In yet another embodiment, a method for forming a bore hole in bone is provided and can include inserting a distal portion of a bone reamer through tissue to position the distal portion of the bone reamer adjacent to bone, rotating one of a first portion and a second portion of a shaft of the bone reamer to thereby rotate one of a first cutting element and a second cutting element disposed on the distal portion of the bone reamer to form a unitary cutting element, and activating a driver coupled to the bone reamer to rotate the bone reamer and thereby cause the unitary cutting element to form a bore hole in the bone. The bone can be, for example, a tibia or femur. In other aspects, inserting the bone reamer through tissue can include positioning a distal end of the bone reamer adjacent to a medial condyle of a femur. In another embodiment, the bone reamer can be advanced over a guidewire.

BRIEF DESCRIPTION OF DRAWINGS

This invention will be more fully understood from the following detailed description taken in conjunction with the accompanying drawings, in which:

FIG. 9A is a top view of one elongate shaft and cutting element of another embodiment of a bone reamer;

FIG. 9B is a cross sectional side view of the elongate shaft and cutting element of FIG. 9A;

FIG. 9C is a top view of an elongate shaft and cutting element that slidably and rotatably mates with the elongate shaft and cutting element of FIGS. 9A and 9B;

FIG. 9D is a cross sectional side view of the elongate shaft and cutting element of FIG. 9C;

DETAILED DESCRIPTION

Figure 1:
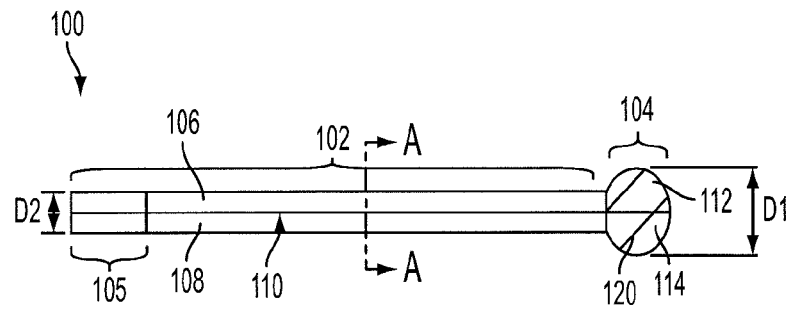
FIG. 1 is a side view of one embodiment of a retractable bone reamer in a non-retracted configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Also, the figures provided herein are not necessarily to scale. In addition, while in some embodiments movement of one component is described with respect to another, a person skilled in the art will recognize that other movements are possible.

Various exemplary low profile retractable bone reamers and methods of use are provided. In general, the retractable bone reamers can allow for drilling a hole, also referred to herein as a bore hole or tunnel, in a bone surface, such as a femur. The retractable reamers described herein can be particularly useful for forming a bone hole along a trajectory that is in close proximity to, or extends through, a body structures such as, e.g., tissue, cartilage, or bone, that are not being operated on. The retractable reamer has a configuration that allows the reamer to be extending along the trajectory while avoiding contact with such body structures, thereby avoiding inadvertent cutting, scraping, or other damage to the body structure(s). In one embodiment, a low profile retractable bone reamer is provided having an elongate shaft with a cutting element disposed on a distal end of the elongate shaft that can be configured to drill a hole in bone. The elongate shaft and cutting element can have first and second longitudinally separated portions, and each of the portions can have a mating surface that can longitudinally slidably couple to the mating surface of the other portion. The reamer can be configured to move between a retracted configuration, in which one portion of the cutting element can be distal of another portion of the cutting element, and a non-retracted configuration, in which both longitudinally separated portions of the cutting element can be positioned adjacent to one another to form a single cutting element. The reamer can therefore be inserted through a surgical portal whose trajectory comes into close proximity with, or even passes through, a body structure that is not being operated on. The cutting element can be advanced up to the body structure, and then the portion positioned farthest from the body structure can be longitudinally advanced past the body structure while the other portion remains in position. The reamer can then be rotated to allow the remaining portion to be advanced past the body structure without contacting the body structure. Once the reamer is in the non-retracted configuration, with both portions positioned past the body structure and aligned with one another, the reamer can be rotated to form a bone hole through bone. The retractable reamers disclosed herein therefore allow for insertion of a surgical bone reamer through a surgical portal whose trajectory comes into close proximity to, or intersects, body structures that are not being operated on, without inadvertently damaging the body structures with the cutting elements disposed on the bone reamer.

The bone reamers disclosed herein can be formed from any one or more materials, preferably a biocompatible material(s) safe for use in the body. In an exemplary embodiment, at least a portion of the reamer can be formed from one or more substantially rigid materials, e.g., titanium, stainless steel, etc. In other embodiments, at least a portion of the reamer, e.g., the elongate shaft, can be formed of one or more flexible materials.

Figure 2:
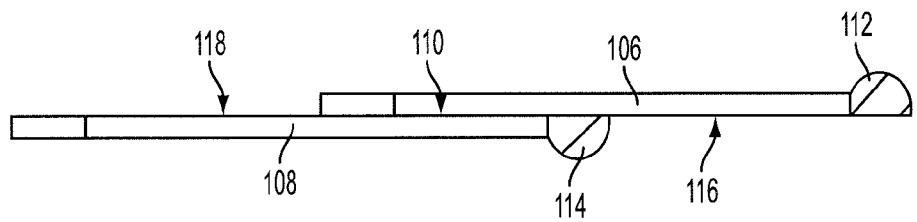
FIG. 2 is a side view of the bone reamer of FIG. 1 in a retracted configuration.
Figure 3:
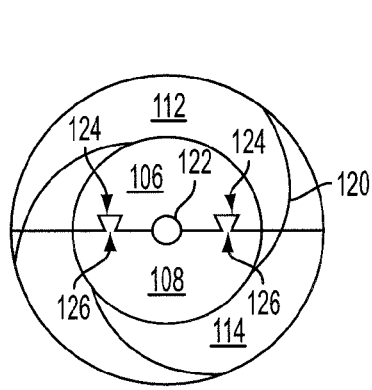
FIG. 3 is a cross sectional end view at section A-A of the bone reamer of FIG. 1.

FIGS. 1-3 illustrate one exemplary embodiment of a low profile retractable bone reamer 100. The reamer 100 can have a variety of sizes, shapes, and configurations. As shown in the illustrated embodiment, the reamer 100 includes an elongate shaft 102 having a cutting element 104 disposed on a distal end thereof that can be configured to drill a hole through bone, and a driver mating portion 105 disposed on a proximal end of the shaft 102 that, as discussed more fully below, can be configured to couple the reamer 100 to a driver and transfer a driving torque from the driver to the reamer 100. The shaft 102 can include first and second portions, e.g., a first elongate shaft 106 and a second elongate shaft 108, and thus the cutting element 104 can likewise include first and second portions, e.g., a first cutting element 112 formed on a distal end of the first elongate shaft 106 and a second cutting element 114 formed on a distal end of the second elongate shaft 108. The first and second elongate shafts 106, 108 can have mating surfaces 116, 118 that are longitudinally slidably coupled along a joint 110 to allow the first and second cutting elements 112, 114 to move between a first position, as shown in FIG. 1, in which the cutting elements 112, 114 are positioned adjacent to one another to form a unitary cutting element 104 that can extend symmetrically about a longitudinal axis extending along and between the first and second elongate shafts 106, 108, and a second position, as shown in FIG. 2, in which the cutting elements 112, 114 are longitudinally offset from one another. The reamer 100 can also include an inner lumen 122 that extends along the entire length of reamer 100 for receiving a guidewire to allow the reamer 100 to be delivered along the guidewire through a surgical portal.

The elongate shaft 102 can have various sizes, shapes, and configurations. In the illustrated embodiment, the elongate shaft 102 is substantially rigid, e.g., formed from one or more substantially rigid materials. In other embodiments, the elongate shaft 102 can be substantially flexible, at least in a direction transverse to a longitudinal axis of the elongate shaft 102, while still being capable of transferring a torsional driving force from a driver coupled to a proximal end of the elongate shaft 102 to the cutting element 104. The length of the elongate shaft 102 can vary widely. In the illustrated embodiment, the shaft 102 is long enough for a proximal end of the shaft 102 to be positioned outside of the body of a patient while the cutting element 104 is positioned adjacent to a bone surface to be drilled within the body of the patient. In other embodiments, the shaft 102 can have a shorter or longer length.

The elongate shaft 102 can have a variety of cross sectional shapes. As shown in FIG. 3, which is a cross sectional view of elongate shaft 102 through section A-A of FIG. 1, the elongate shaft 102 has a substantially circular cross sectional shape. The first elongate shaft 106 and the second elongate shaft 108 can thus each have a substantially semi-circular cross sectional shape. The shaft 102 can have a variety of other cross sectional shapes, including square, triangular, or elliptical. The first and second elongate shafts 106, 108 can also have a variety of cross sectional shapes and sizes, for example, either the first elongate shaft 106 or the second elongate shaft 108 can comprise more than half of the cross sectional area of the shaft 102 and the first mating surface 116 and second mating surface 118 can have any number of configurations that allow first and second elongate shafts 106, 108 to be longitudinally slidably coupled.

As indicated above, the reamer 100 can also include an inner lumen 122 extending therethrough for receiving a guidewire. In the illustrated embodiment, the lumen 122 is formed from opposing recesses formed in the first and second mating surfaces 116, 118, the recesses extending along the entire length of reamer 100. In other embodiments, the lumen 122 can be formed completely within the first or second elongate shaft 106, 108.

In the illustrated embodiment, the mating surface 116 of the first elongate shaft 106 also has two female mating elements 124 that are configured to slidably couple with two male mating elements 126 formed on the mating surface 118 of the second elongate shaft 108. Each of the female mating elements 124 can form a dovetail joint with a corresponding male mating element 126. While two female mating elements 124 and two male mating elements 126 are illustrated, any number of pairs of male and female mating elements 126, 124 can be used and can be located anywhere along first and second mating surfaces 116, 118. As further shown in FIG. 3, the female and male mating features 124, 126 are located at approximately the mid-point between the guidewire lumen 122 and the outer wall of elongate shaft 102 to provide a coupling that balances the centrifugal forces exerted on the reamer 100 during use. In other embodiments, the mating features 124, 126 can be located at other locations. In some embodiments, additional mating features can be located in the first and second cutting elements 112, 114, for example, at a location lateral to the outer diameter of elongate shaft 102 to provide a more secure coupling of the first and second cutting elements 112, 114. While the illustrated embodiment includes dovetail joints with male and female mating elements, this is for illustrative purposes only, and any other mechanism for longitudinally slidably coupling first and second elongate shafts 106, 108 can be used. For example, in another embodiment, instead of, or in addition to mating elements on a mating surface of the first and second elongate shafts, the first and second elongate shafts can be slidably disposed within an outer cannula (not shown), where the outer cannula longitudinally slidably couples the first and second elongate shafts. One of the first and second elongate shafts can also be non-removably fixed to the outer cannula and the other elongate shaft can be slidably disposed within the cannula so that the reamer can move between a retracted and non-retracted configuration.

In the illustrated embodiment, the mating elements 124, 126 extend along the entire length of the elongate shaft 102 and the cutting element 104, which can allow the entire length of the first elongate shaft 106 and the first cutting element 112 to be slidably coupled to the entire length of the second elongate shaft 108 and the second cutting element 114. Having mating elements extend along the entire length of the shaft 102 and the cutting element 104 can help ensure a secure coupling between the first and second elongate shafts 106, 108 and the first and second cutting elements 112, 114 and prevent any centrifugal forces acting on the reamer 100 during the drilling process from separating or "splaying" apart the first and second shafts 106, 108 and/or first and second cutting elements 112, 114. In other embodiments, the mating features can extend along less than the entire length of the reamer 100. For example, the first and second elongate shafts 106, 108 can have a plurality of mating elements located along the length of the reamer 100, for example, a plurality of pairs of male and female mating elements can be located along the length of reamer 100. As will be discussed more fully below, in embodiments where the mating elements do not extend along the entire length of the reamer, at least one of the plurality of mating elements can have a length that is at least as long as the distance the reamer will be retracted during use, which can ensure the first and second portions of the reamer remain coupled when the reamer is moved to a retracted configuration.

Figure 4:
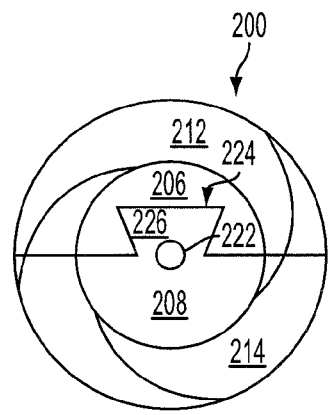
FIG. 4 is a cross sectional end view at section A-A of another embodiment of a retractable bone reamer.
Figure 5:
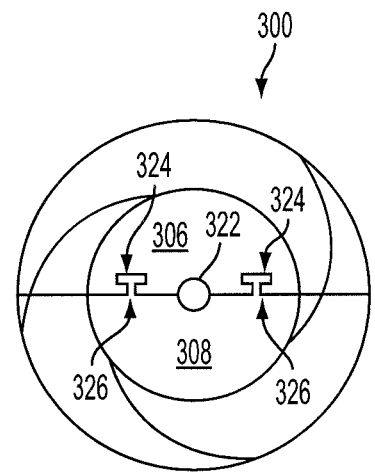
FIG. 5 is a cross sectional end view at section A-A of yet another embodiment of a retractable bone reamer.

FIGS. 4 and 5 illustrate alternative embodiments of mating elements. FIG. 4 illustrates an embodiment of a reamer 200 where a first elongate shaft 206 and a second elongate shaft 208 are slidably coupled with a mating element in the form of single dovetail joint. The reamer 200 can generally be configured and used similar to other reamers disclosed herein with like-named elements. In the illustrated embodiment, the reamer 200 has a single female mating feature 224 located on a mating surface of the first elongate shaft 206 that is configured to be longitudinally slidably coupled to a male mating feature 226 located on a mating surface of the second elongate shaft 208. Similar to reamer 100, a guidewire lumen 222 extends along the entire length of reamer 200 through the male mating feature 226. Also similar to reamer 100, the female and male mating features 224, 226 can extend along the entire length of reamer 200, which can improve the coupling of first and second elongate shafts 202, 204. In other embodiments, the reamer 200 can have a plurality of pairs of male and female mating features 226, 224 that can be located along the length of the reamer 200. In the illustrated embodiment, the single dovetail joint formed from the female and male mating features 224, 226 is located approximately at the center of reamer 200 to provide a coupling that balances the centrifugal forces exerted on the reamer 200 during use. In other embodiments, the mating features can be located at a location other than approximately at the longitudinal center of reamer 200. Similar to reamer 100, first and second cutting elements 212, 214 can include additional mating features that can be, for example, located lateral to the outer surface of elongate shaft 202 to provide a more secure coupling of first and second cutting elements 212, 214.

FIG. 5 illustrates an embodiment of a reamer 300 where a first elongate shaft 306 and a second elongate shaft 308 are slidably coupled with two t-shaped joints. The reamer 300 can generally be configured and used similar to other reamers disclosed herein with like-named elements. In the illustrated embodiment, the reamer 300 has two female mating features 324 located on a mating surface of the first elongate shaft 306 that are configured to be longitudinally slidably coupled to respective male mating features 326 located on a mating surface of the second elongate shaft 308. The mating features can vary, as discussed above with respect to reamers 100 and 200. Moreover, the reamer 300 can also include other features discussed herewith with respect to reamer 100, such as a guidewire lumen 322 extending along the entire length of reamer 300.

Referring back to FIGS. 1-3, the reamer 100 also includes a cutting element 104. While the cutting element 104 can have a variety of configurations, in the illustrated embodiment, the cutting element 104 has a substantially bulbous shape that is substantially symmetrical about a longitudinal axis of shaft 102. As discussed above, the cutting element 104 can separate longitudinally into a first cutting element 112 and a second cutting element 114 that are slidably coupled along the first and second mating surfaces 116, 118. In the illustrated embodiment, the cutting element 104 has a maximum outer diameter D1 that is greater than a maximum outer diameter D2 of the shaft 102 such that the first cutting element 112 is offset from a central axis of the first elongate shaft 106 and the second cutting element 114 is offset from a central axis of the second elongate shaft 108. The diameter D2 of cutting element 104 can vary, for example, depending on the surgical procedure and the desired diameter of the hole to be drilled in bone. The cutting element 114 is shown with a bulbous shape for illustrative purposes only and the cutting element can have a variety of other shapes and sizes. For example, the cutting element can taper radially inward at a distal-most end to form a pointed tip. For another example, the unitary cutting element can have a shape and size that approximates the shape and size of the cutting portions of any prior art bone reamer, including any prior art "acorn reamer."

Figure 6:
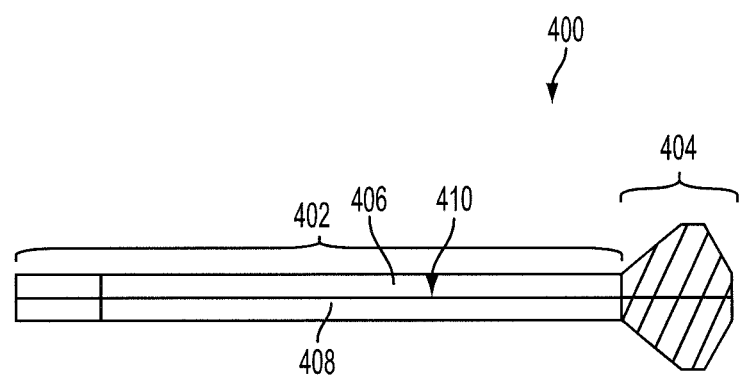
FIG. 6 is a side view of another embodiment of a bone reamer shown in a non-retracted configuration.
Figure 7A:
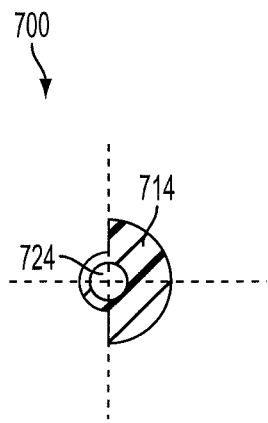
FIG. 7A is a top view of one elongate shaft and cutting element of a bone reamer.
Figure 7C:
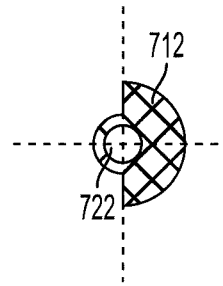
FIG. 7C is a top view of an elongate shaft and cutting element that slidably and rotatably mates with the elongate shaft and cutting element of FIGS. 7A and 7B.
Figure 7B:
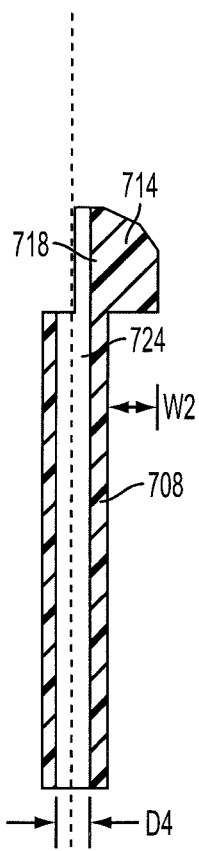
FIG. 7B is a cross sectional side view of the elongate shaft and cutting element of FIG. 7A.
Figure 7D:
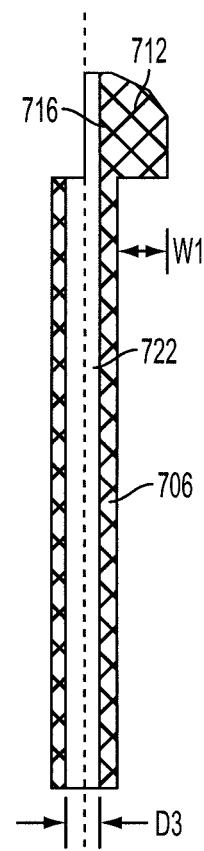
FIG. 7D is a cross sectional side view of the elongate shaft and cutting element of FIG. 7C.

By way of non-limiting example, FIG. 6 illustrates an embodiment of a reamer 400 with a non-bulbous cutting element 404. The reamer 400 can generally be configured and used similar to other reamers disclosed herein with like-named elements. Similar to reamers 100-300, the first and second elongate shafts 406, 408 and the first and second cutting elements 412, 414 can be configured to be longitudinally slidably coupled along a joint 410 so that the reamer 400 can move between a retracted position, where either the first or second cutting element 412 or 414 is proximal of the other cutting element 412 or 414 and a non-retracted position, where the first and second cutting elements 412 and 414 can be positioned adjacent to one another to form a unitary cutting element 404 that can extend symmetrically about a longitudinal axis extending between the first and second cutting elements 412 and 414. In the illustrated embodiment, the reamer 400 has a non-bulbous cutting element 404, where a proximal portion of the cutting element 404 tapers radially outward to an intermediate portion, and a distal portion tapers radially inward to a distal end. In other embodiments, the reamer 400 can have a variety of other non-bulbous shapes and configurations. For example, the cutting element can taper radially inward at a distal-most end to form a pointed tip. A maximum outer diameter of the cutting element 404 can also vary widely from less than a maximum outer diameter of the elongate shaft 402 to greater than a maximum outer diameter of elongate shaft 402. As will be appreciated by a person having ordinary skill in the art, the shape and size of cutting element 404 can vary depending on a variety of factors, including the type of bone being drilled, the desired size of the hole to be drilled in bone, the rotational speed the reamer will be operated at, and the desired rate of bone removal.

As further shown in FIGS. 1-3, the cutting element 104 can also include cutting features, such as flutes 120, for cutting bone. While the flutes 120 can have a variety of configurations, in the illustrated embodiment the flutes 120 are in formed from a plurality of parallel grooves that are formed around portions of an outer surface of the cutting element 104. The flutes 120 can have various profiles, including a sharpened edge or a square-thread profile. The sharpened edges can provide a cutting surface for cutting into bone. The grooves formed by the flutes 120 can provide a pathway for bone fragments cut away from bone by the flutes 120 to be transported proximally and away from a hole in bone being drilled by the cutting element 104. The flutes 120 can be formed at any angle with respect to a longitudinal axis of shaft 102. In an exemplary embodiment, the flutes 120 on the first and second cutting elements 112, 114 are aligned when the cutting elements 112, 114 are aligned. In other embodiments, flutes 120 can be formed completely in either the first cutting element 112 or the second cutting element 114.

As indicated above and as shown in FIGS. 1-2, the reamer 100 can be configured to be movable between a retracted position wherein the reamer 100 has a smaller width at the distal end, and a non-retracted position wherein the reamer has a larger width or diameter at the distal end and is configured to drill a hole through bone. FIG. 1 illustrates an exemplary embodiment of the reamer 100 in a non-retracted position, with the first elongate shaft 106 and second elongate shaft 108 being longitudinally slidably coupled and the first cutting element 112 and the second cutting element 114 being aligned and positioned adjacent to one another to form unitary cutting element 104. FIG. 2 illustrates an exemplary embodiment of the reamer 100 in a retracted position, wherein the first elongate shaft 106 and the second elongate shaft 108 are longitudinally slidably coupled and the first cutting element 112 is positioned distal of the second cutting element 114. The first and second elongate shafts 106, 108 can also be slid relative to each other in the opposite direction so that the first cutting element 112 can be positioned proximal of the second cutting element 114. The reamer 100 can be movable between the retracted position and the non-retracted position by sliding the first and second elongate shafts 106, 108 relative to one another along the first and second mating surfaces 116, 118. In the retracted position, the distal-most cutting element, e.g., the first cutting element 112, will have a width that is equal to the radius of one of the first cutting element. As a result, the first cutting element 112 will have a lower profile and can be passed through a restricted passageway. In the non-retracted position, the first and second cutting elements 112, 114 are aligned and as a result have an enlarged outer width or diameter. In this position, the cutting elements are configured to form a bone hole.

In some embodiments, the reamer 100 can also include locking features (not shown) that can aid in determining when the reamer 100 is positioned in the non-retracted configuration, and can also aid in maintaining the reamer 100 in the non-retracted configuration. For example, the first mating surface 116 can have one or more protrusions (not shown) that can align with one or more recesses in the second mating surface 118 (not shown) when the first and second elongate shafts 106, 108 are aligned in the non-retracted configuration.

In some embodiments the locking features can provide a mechanical response and/or an audible response, such as a "click," to indicate the reamer 100 is in the non-retracted position, and can provide a mechanical and/or frictional coupling that can maintain the reamer 100 in the non-retracted position, for example, when the reamer 100 is being used to drill a hole in a bone. A variety of other locking features can be used, including a frictional or interference fit between portions of the first and second mating surfaces 116, 118, or a locking pin that can be slidably engaged with recesses or holes formed in the first and second elongate shafts 106, 108.

FIGS. 7A-10B illustrate alternative embodiments of retractable bone reamers having a first elongate shaft that is rotatably and slidably disposed within a second elongate shaft. FIGS. 7A-8B illustrate a retractable reamer 700, which can generally be configured and used similar to other reamers disclosed herein with like-named elements. Similar to reamers 100-400, the first and second elongate shafts 706, 708 and the first and second cutting elements 712, 714 can be configured to be longitudinally slidably coupled so that the reamer 700 can move between a retracted position and a non-retracted position. The first and second elongate shafts 706, 708 can be cannulated, with the first elongate shaft having an inner lumen 722 extending along the length of the first elongate shaft 706, and the second elongate shaft having an inner lumen 724 extending along the length of the second elongate shaft 708. The first elongate shaft 706 can have a maximum outer diameter D3 that is less than a minimum inner diameter D4 of the inner lumen 724 in the second elongate shaft so that, as discussed more fully below, the first elongate shaft 706 can be rotatably and slidably disposed within the inner lumen 724 of the second elongate shaft 708.

Similar to the reamers 100-400, reamer 700 can have a first cutting element 712 disposed on the distal end of the first elongate shaft 706 and a second cutting element 714 disposed on the distal end of the second elongate shaft 708. The first and second cutting elements 712, 714 can be offset from a central longitudinal axis of the reamer 700 so that, as discussed more fully below, the reamer 700 can be positioned in a low-profile retracted configuration. In the illustrated embodiment, the outer second elongate shaft 708 terminates just proximally of the second cutting element 714 which, as illustrated in FIG. 8B, allows the first cutting element 712 to nest against the distal end of the outer second elongate shaft 708 and be positioned opposite of the second cutting element 714. In the illustrated embodiment, the inner first elongate shaft 706 terminates just proximal of the first cutting element 714. In alternative embodiments, the inner first elongate shaft can extend along the entire length of the reamer 700 and terminate at the distal end of the first cutting element 712.

The inwardly-facing surface 716 of the first cutting element 712 and the inwardly-facing surface 718 of the second cutting element 714 can each be generally concave to define a hollow hemi-cylindrical cavity. As a result when the first and second cutting elements 712, 714 are aligned, the hemi-cylindrical cavities of the inwardly-facing surfaces 716, 718 can form an extension of the inner lumen 722 for allowing a guidewire 726 (shown in FIGS. 8A and 8B) to extend through. The outwardly facing surfaces of the first and second cutting elements 712, 714 can each have a convex shape such that each cutting element is substantially hemi-cylindrical when viewed from the end. When mated together, the first and second cutting elements 712, 714 can form a unitary cutting element that has a substantially cylindrical shape that is substantially symmetric about a longitudinal axis of the reamer 700. The unitary cutting element can have a rounded distal tip and a truncated proximal end that extends approximately orthogonal to an outer wall of the first and second elongate shafts 706 and 708. The shape of the first and second cutting elements 712, 714 in FIGS. 7A-8B is for illustrative purposes only and the first and second cutting elements 712, 714 can have any shape that allows the reamer 700 to be used to drill a hole through bone. In an exemplary embodiment, the first cutting element 712 has a width W1 measured from an outer edge of the first cutting element 712 to an outer sidewall of the first elongate shaft 706 that is greater than a width W2 of the second cutting element 714 measured from an outer edge of the second cutting element 714 to an outer sidewall of the second elongate shaft 708. As discussed more fully below, by configuring the first cutting element 712 with a width W1 that is greater than the width W2 of the second cutting element 714, the first and second cutting elements 712, 714 can form a unitary cutting element that extends symmetrically about a central longitudinal axis of the reamer 700, despite the second elongate shaft 708 having a greater outer diameter than the first elongate shaft 706. In alternative embodiments, the width W1 of the first cutting element 712 can be the same as or less than the width W2 of the second cutting element 714.

Figure 8A:
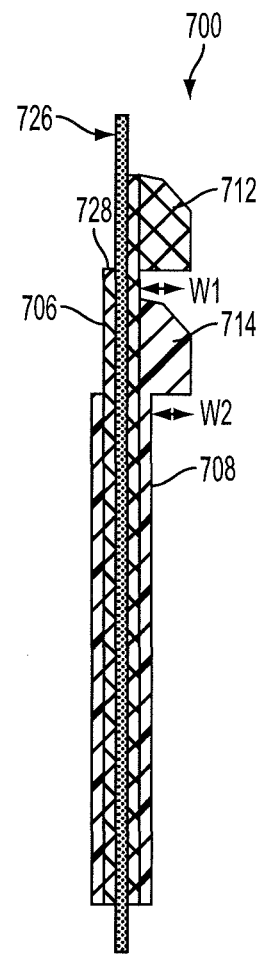
FIG. 8A is a cross sectional side view of the bone reamer of FIGS. 7A-7D in a retracted configuration.
Figure 8B:
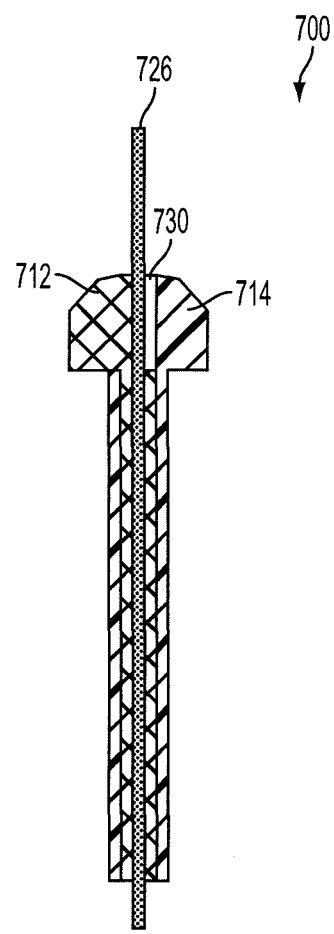
FIG. 8B is a cross sectional side view of the bone reamer of FIGS. 7A-7D in a non-retracted configuration.

FIGS. 8A and 8B illustrate the reamer 700 assembled, where the first elongate shaft 706 is slidably and rotatably disposed within the inner lumen 724 of the second elongate shaft 708. In particular, FIG. 8A illustrates the reamer 700 in a retracted configuration and FIG. 8B illustrates the reamer 700 in a non-retracted configuration. As shown in FIGS. 8A and 8B, the reamer 700 can be slid over a guidewire 726 by passing the guidewire 726 through the inner lumen 722 of the first elongate shaft 706.

As shown in FIG. 8A, the reamer 700 can be positioned in a retracted configuration, where the first elongate shaft 706 is disposed within the inner lumen 724 of the second elongate shaft 708, and the first cutting element 712 is positioned distal of the second cutting element 714. In the retracted configuration, the first and second cutting elements 712, 714 can be circumferentially aligned so that the first and second cutting elements 712, 714 are both positioned on the same side of the reamer 700. Because the width W1 of the first cutting element 712 is greater than the width W2 of the second cutting element 714, the outer edges of the first and second cutting elements 712, 714 can extend approximately the same radial distance from the central longitudinal axis of the reamer 700 despite the second elongate shaft 708 having a greater outer diameter than the first elongate shaft 706. With the first and second cutting elements 712, 714 positioned on the same side of the reamer 700, a distal end of the reamer 700 can have a lower profile and a reduced width, which facilitates passing the reamer 700 though a narrow passageway without inadvertently scraping the walls of the narrow passageway with either of the first or second cutting elements 712, 714.

Reamer 700 can be repositioned between the retracted configuration shown in FIG. 8A, and the non-retracted configuration shown in FIG. 8B, by rotating the first cutting element 712 relative to the second cutting element 714, e.g., approximately 180 degrees, so that the first and second cutting elements 712, 714 are positioned on opposite sides of the reamer 700. The second cutting element 714 and second elongate shaft 708 can be slid distally relative to the first cutting element 712 to position the first and second cutting elements 712, 714 adjacent to one another to form a unitary cutting element. The reamer 700 in the non-retracted position can have a larger width at a distal end then when the reamer 700 is in the retracted configuration, and can thus be configured to drill a hole in bone.

Figures 10A, 10B:
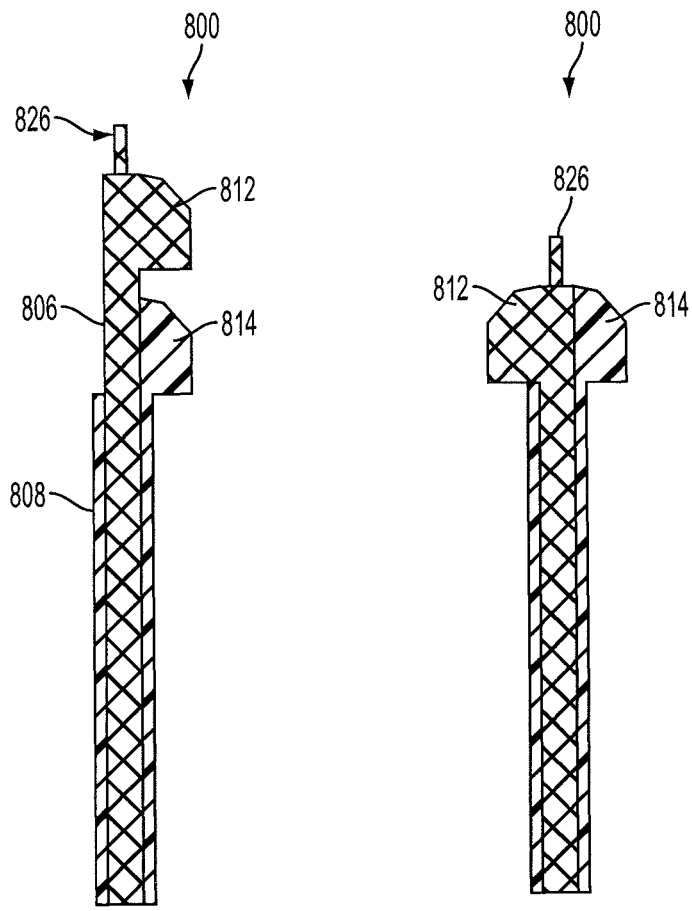
FIG. 10A is a cross sectional side view of the bone reamer of FIGS. 9A-9D in a retracted configuration.
FIG. 10B is a cross sectional side view of the bone reamer of FIGS. 9A-9D in a non-retracted configuration.

FIGS. 9A-10B illustrate another exemplary embodiment of a retractable reamer 800, similar to the retractable reamer illustrated in FIGS. 7A-8B. Instead of having a cannulated first elongate shaft that a guide wire can be passed through, the reamer 800 has a solid, non-cannulated first elongate shaft 806 and a solid first cutting element 812. The first cutting element 812 can also have a guide 826 extending distally therefrom that can, for example, be coupled to other devices used to guide the reamer 800 through a surgical portal, and can also be used to properly align the reamer 800 with a pre-drilled hole in bone. Similar to the reamer 700, the first elongate shaft 806 can be slidably and rotatably disposed within an inner lumen 824 of a second elongate shaft 808 so that, as illustrated in FIGS. 10A and 10B, the reamer 800 can be positioned in a low-profile retracted configuration, and in a wider-profile non-retracted configuration.

Figures 11A, 11B:
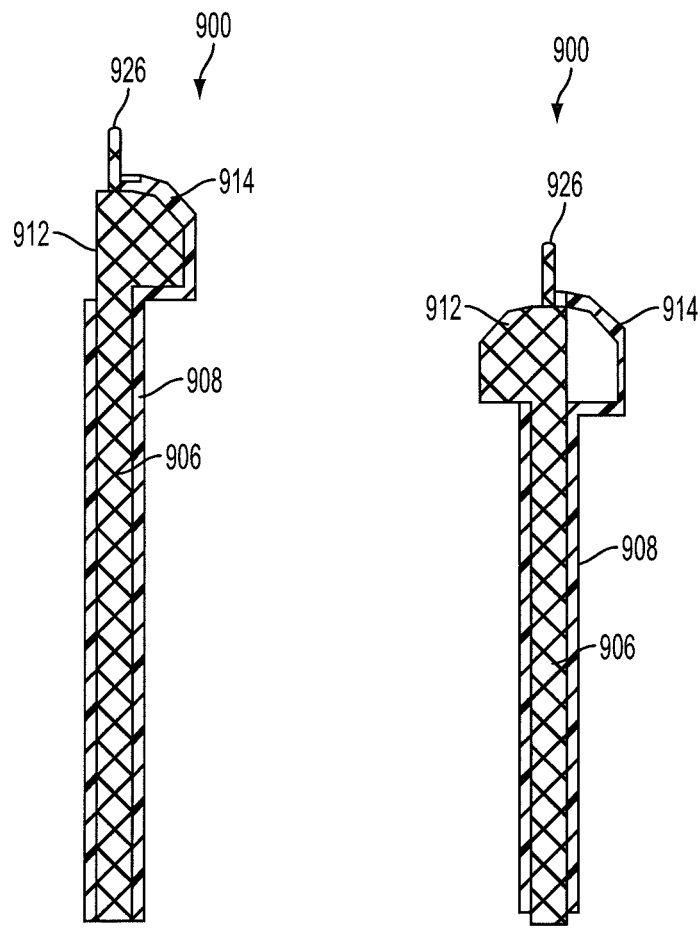
FIG. 11A is a is a cross sectional side view of another embodiment of a retractable bone reamer illustrated in a retracted configuration.
FIG. 11B is a is a cross sectional side view of the bone reamer of FIG. 11A in a non-retracted configuration.

FIGS. 11A and 11B illustrate another exemplary embodiment of a retractable reamer 900, where a first portion is rotatably coupled to a second portion. In particular, the reamer 900 includes a first elongate shaft 906 and a first cutting element 912 that is rotatably disposed within a second elongate shaft 908 and a second cutting element 914. The second elongate shaft 908 can be cannulated and can have an inner lumen extending therethrough, and the inner lumen can have a minimum inner diameter that is greater than a maximum outer diameter of the first elongate shaft 912. The first elongate shaft 912 can thus be rotatably disposed within the inner lumen of the second elongate shaft so that, as discussed more fully below, the reamer 900 can be positioned between a low profile retracted configuration and a wider profile non-retracted configuration. A first cutting element 912 can be positioned on the distal end of the first elongate shaft 906, and can have a substantially hemi-cylindrical shape. The first cutting element 912 can also have a guide 926 disposed on a distal end of the first cutting element 912. Similar to guide 826, guide 926 can, for example, be coupled to other devices used to guide the reamer 900 through a surgical portal, and can also be used to properly align the reamer 900 with a pre-drilled hole in bone. The guide 926 can also be used to rotatably couple the first cutting element 912 to the second cutting element 914. The second cutting element 914 can be positioned on the distal end of the second elongate shaft 908 and can also have a substantially hemi-cylindrical shape. As shown in FIGS. 11A and 11B, the second cutting element 914 can be a hollow shell with an inner volume configured to rotatably receive the first cutting element 912 therein, and the second cutting element 914 can have an outer surface that is sized and configured to cut a hole in bone. The first cutting element 912 can have a width that is less than a width of the second cutting element 914 so that the first cutting element 912 can be disposed within the second cutting element 914.

As shown in FIGS. 11A and 11B, the reamer 900 can be positioned between a retracted configuration, as illustrated in FIG. 11A, and a non-retracted configuration, as illustrated in FIG. 11B. In the retracted configuration, the first cutting element 912 can be positioned in substantially the same circumferential position, i.e., axially aligned, as the second cutting element 914 to thereby position the first cutting element 912 within the inner space of the hollow second cutting element 914. In the retracted configuration, the distal end of the reamer 900 can therefore have a reduced, or lower profile that can allow the reamer 900 to be passed though a narrow passageway without inadvertently scraping the walls of the narrow passageway with either of the first or second cutting elements 912 or 914. The reamer 900 can move between the retracted configuration and the non-retracted configuration by rotating either the first elongate shaft and the first cutting element 906, 912 or the second elongate shaft and the second cutting element 908, 914 approximately 180 degrees relative to the other elongate shaft and cutting element to thereby position the first and second cutting elements 912, 914 on opposite sides of the reamer 900. With the first and second cutting elements 912, 914 positioned on the opposite sides of the reamer 900, the first and second cutting elements 912, 914 can form a unitary cutting element that is substantially symmetric about a central longitudinal axis of the reamer 900 that can be configured to cut a hole in bone. The reamer 900 has the advantage of being movable between the retracted and non-retracted configurations with a single rotational motion and without the need for any additional sliding motion between the first and second elongate shafts, which can result in simplified surgical procedures. To improve the coupling between the first and second cutting elements 912, 914, the guide 926 can be rotatably disposed through an opening (not shown) in the distal end of the second cutting element 914. Having the guide 926 positioned within and extending through an opening in the distal end of the second cutting element 914 can improve the coupling between the first and second cutting elements 912, 914. As with any of the reamers disclosed herein, the reamer 900 can also include locking features that can, for example, enable the reamer 900 to securely remain in the non-retracted configuration during drilling. And as with any of the other reamers disclosed herein, the shape of the first and second cutting elements 912, 914 in the illustrated embodiment are for illustrative purposes only, and the first and second cutting elements 912, 914 can have any number of shapes or geometries that allow them to form a unitary cutting element and be configured to cut a hole in bone.

Figure 12:
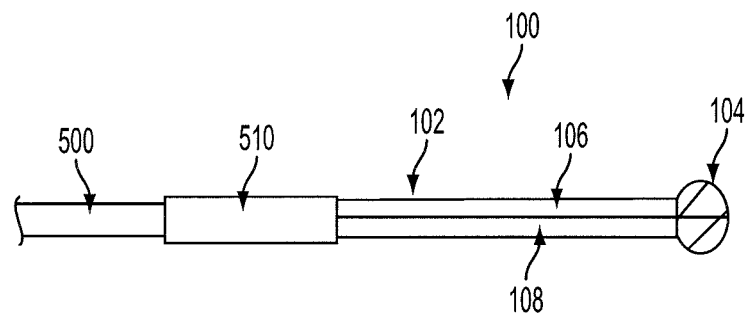
FIG. 12 is a side view of the bone reamer of FIG. 1 coupled to a driver with a collar.
Figure 13:
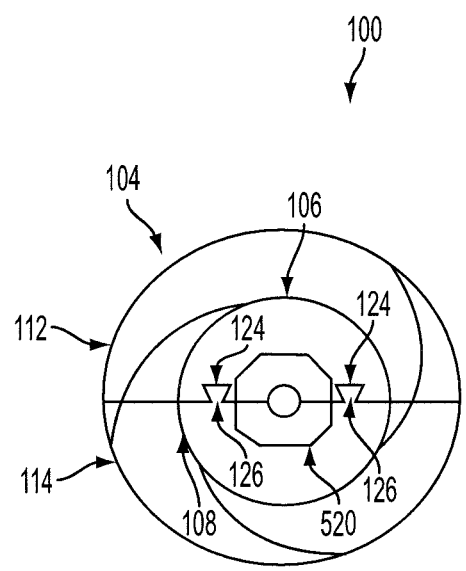
FIG. 13 is an end view of the bone reamer of FIG. 1.

FIGS. 12-13 illustrate an exemplary embodiment of a device for coupling a reamer to a driver. While FIGS. 12-13 are discussed with reference to reamer 100 of FIGS. 1-3, the coupling devices discussed herein and any other coupling device can be used with any of the reamers discussed herein. As shown in the illustrated embodiment, a distal end of a driver 500 can be coupled to a proximal end of the reamer 100 by a collar 510. In an exemplary embodiment, the collar 510 is a substantially cylindrical member with an inner lumen that the driver 500 and the elongate shaft 102 can be disposed within. The collar 510 can be removably coupled to both the distal end of the driver 500 and the proximal end of the reamer 100, or the collar 500 can be non-removably fixed to either the driver 500 or the reamer 100. In a preferred embodiment, the collar 510 is non-removably fixed to the driver 500, and a proximal end of the reamer 100 can be slidably disposed within the collar 510, thereby coupling collar 510 to reamer 100. In the illustrated embodiment, the inner lumen of the collar has torque transfer features (not shown) that couple to features on the outer surface of elongate shaft 102 so that in use, the collar 510 can transfer a driving torque from the driver 500 to the reamer 100 to rotate the reamer 100 and drill a hole with the cutting element 104 in bone. A person having ordinary skill in the art will appreciate that the torque transfer features can be formed from a variety of devices. For example, a proximal portion of the elongate shaft 102 can have a non-circular shape, such as a hexagonal shape that is configured to mate with a complementary and similarly sized and shaped portion of the inner lumen of the collar 510. For another example, the collar can have a protrusion that slidably engages with a recess or channel in the elongate shaft that can prevent relative rotational motion between the collar 510 and the shaft 102. In other embodiments, the collar 510 can have no torque transfer features, so that the collar does not transfer torque from the driver 500 to the reamer 100, and the collar 510 can instead be used to properly align driver 500 with reamer 100.

FIG. 13 is an end view of the elongate shaft 102 and driver mating portion 105. In the illustrated embodiment, in addition to the collar 510, the reamer 100 has driver mating portion 105 that can couple to a distal end of driver 500. The driver mating portion 105 includes a recess 520 that is configured to slidably couple with a male driver feature (not shown) at a distal end of driver 500. The recess 520 is formed from recesses in proximal portions of the mating surfaces 116, 118 of the first and second elongate shafts 106, 108. In use, a male driver feature at a distal end of the driver 500 that has a complementary size and shape to the recess 520 can be slidably disposed within the recess 520 and can thereby transfer a driving torque from the driver 500 to the reamer 100. While the driver mating portion 105 includes an octagon-shaped recess 520, this is for illustrative purposes only and a variety of other devices can be used to transfer torque from the driver 500 to the reamer 100. For example, the recess 520 can have a different shape, or the driver mating portion 105 can have a male member that can be slidably disposed and non-rotatably coupled within a female member formed in a distal portion of the driver 500.

FIGS. 14-17 illustrate an exemplary method for advancing a retractable bone reamer through a surgical portal and positioning a distal end of the reamer adjacent to a bone surface to be drilled. While FIGS. 14-17 show advancing a bone reamer through an anterior medial ("AM") portal in a left knee to drill a femoral tunnel as part of ACL reconstruction surgery, the methods and devices disclosed herein could be used at a variety of anatomical locations and in a variety of medical procedures in which a hole is drilled through bone. Additionally, although FIGS. 14-17 are discussed with reference to reamer 100 of FIGS. 1-3, any of the reamers discussed herein can be implemented in this or other ways.

The surgical procedure can include preparing a patient for surgery using standard techniques. In a minimally invasive procedure, one or more introducer devices (not shown), e.g., a cannula, a trocar, etc., can be advanced through an AM portal in the patient to provide access to a surgical site. A person having ordinary skill in the art will appreciate that one or more viewing devices, e.g., a scoping device such as an endoscope, can be advanced into the body through the incision or through another opening, e.g., another incision or a natural orifice, to provide visualization of the surgical site from outside the body. With the AM portal located, a guide pin can be drilled into a lateral condoyle 610 of a femur 600 according to ACL reconstruction procedures known in the art. A distal end of a guidewire can be coupled to the guide pin and a proximal portion of the guidewire can extend through the AM portal to a location outside of the body of the patient. For clarity, FIGS. 14-17 show a reamer 100 and the distal end of a femur 600 and omit the guide pin, guidewire, and other anatomical structures.

Figure 14:
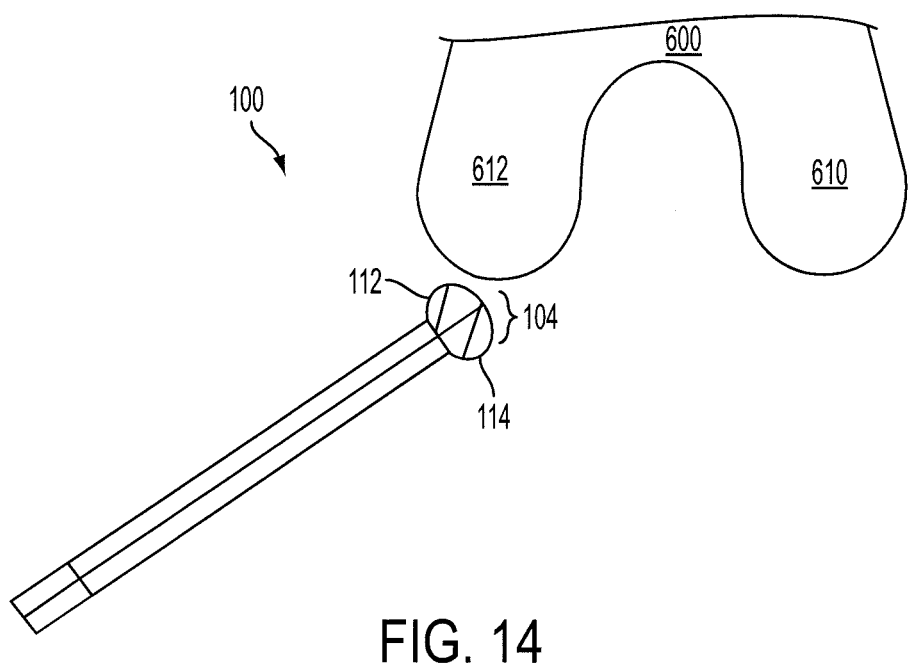
FIG. 14 is a side view of the bone reamer of FIG. 1 in a non-retracted configuration positioned in an anterior medial surgical portal adjacent to a medial condoyle of a femur.

As shown in FIG. 14, the reamer 100 can be advanced through an AM portal along a guide wire (not shown) slidably disposed within the inner lumen 122 of the reamer 100. The reamer can be advanced until the cutting element 104 is positioned adjacent to a medial condoyle 612 of a femur 600. Advancing a reamer through the AM portal to form a femoral tunnel on the femoral notch is desirable because it results in a more anatomical ACL reconstruction. As shown in FIG. 14, in the approach to the femoral notch and lateral condoyle, the trajectory of the AM portal can come into close proximity with an articulating surface of the medial condoyle 612. In the illustrated embodiment, the reamer 100 is initially advanced through the AM portal in the non-retracted position. This is for exemplary purposes only, and the reamer 100 can also be advanced through the AM portal in a retracted position with either the first cutting element 112 or the second cutting element 114 distal of the other cutting element 112 or 114. As shown in the illustrated embodiment, advancing the reamer 100 through the AM portal can place the reamer 100 on a trajectory where the cutting element 104 could come into contact with the articulating surface of the medial condoyle 612 if it is advanced beyond the position of the reamer 100 shown in FIG. 14.

Figure 15:
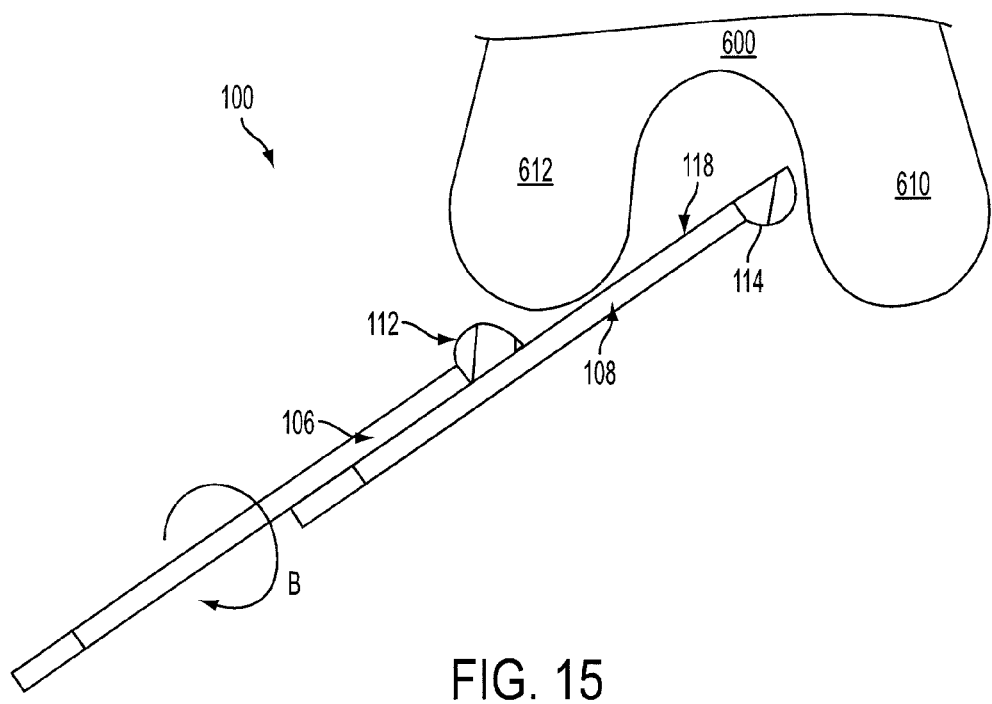
FIG. 15 is a side view of the bone reamer and femur of FIG. 14 with the reamer in a retracted configuration, with one portion of a cutting element positioned adjacent to a lateral condoyle of the femur and another portion of a cutting element positioned adjacent to the medial condoyle of the femur.

As shown in FIG. 15, to avoid inadvertently scraping, cutting, or otherwise damaging the articulating surface of the medial condoyle 612, the reamer 100 can be moved to a retracted configuration, whereby the second elongate shaft 108 and second cutting element 114 are slid distally relative to the first elongate shaft 106 and first cutting element 112. As shown in FIG. 15, by moving the reamer 100 to the retracted position by advancing only the second elongate shaft 108 and second cutting element 114, the reamer 100 can be advanced further through the AM portal along the guidewire (not shown) until the second cutting element 114 is adjacent to the lateral condoyle 610 in the femoral notch. By advancing only the second elongate shaft 108 and second cutting element 114 past the medial condoyle 612, the reamer 100 will have a low profile and can be brought into very close proximity to the medial condoyle 612 without cutting or scraping an articulating surface of the medial condoyle 612. The reamer 100 can be brought into close proximity because the second cutting element 114 can positioned away from the medial condoyle 612 and the mating surface 118 can be positioned towards the medial condoyle 612. This can allow the reamer 100 to be advanced through an AM portal with a trajectory that comes closer to the medial condoyle 612 because the overall width of the cutting element is reduced. The reamer 100 can therefore be safely passed in close proximity to the medial condoyle 612.

As shown in FIG. 15, in the illustrated embodiment, the reamer 100 can retract a distance sufficient to allow one cutting element to be positioned adjacent to a medial surface of the lateral condoyle while the other cutting element is positioned adjacent to a medial surface of the medial condoyle. In a preferred embodiment, this can generally be the minimum distance the reamer 100 can retract. The length of the elongate shaft 102 can be selected to provide for this minimum retracted distance. In embodiments where mating features, such as mating features 124, 126, do not extend along the entire length of the reamer 100, for example in embodiments where there are a plurality of mating features disposed along a longitudinal axis of the reamer 100, the length of one or more of the mating features can be at least as long as the distance from the medial side of the medial condoyle to the medial side of the lateral condoyle. This can allow the reamer 100 to move to a retracted position while maintaining a coupling between first elongate shaft 106 and second elongate shaft 108.

As mentioned above, in the illustrated embodiment, the reamer 100 is initially advanced in a non-retracted position and then moved to a retracted position to advance the second elongate shaft 108 and second cutting element 114 past the medial condoyle 612. This is for illustrative purposes only. In other embodiments, where first cutting element 112 is positioned away from medial condoyle 612, the reamer 100 can be moved to a retracted position by distally advancing the first elongate shaft 106 and first cutting element 112. In yet another embodiment, the reamer 100 can be initially advanced through the AM portal in a retracted configuration with either the first cutting element 112 or second cutting element 114 distal of the other cutting element 112 or 114. In embodiments where the reamer 100 is initially advanced through the AM portal in a retracted configuration, the more-distal cutting element can be advanced past the medial condoyle 612 with the cutting element positioned away from the medial condoyle 612 without first having to retract the reamer 100, because the reamer 100 is already in a retracted configuration.

Figure 16:
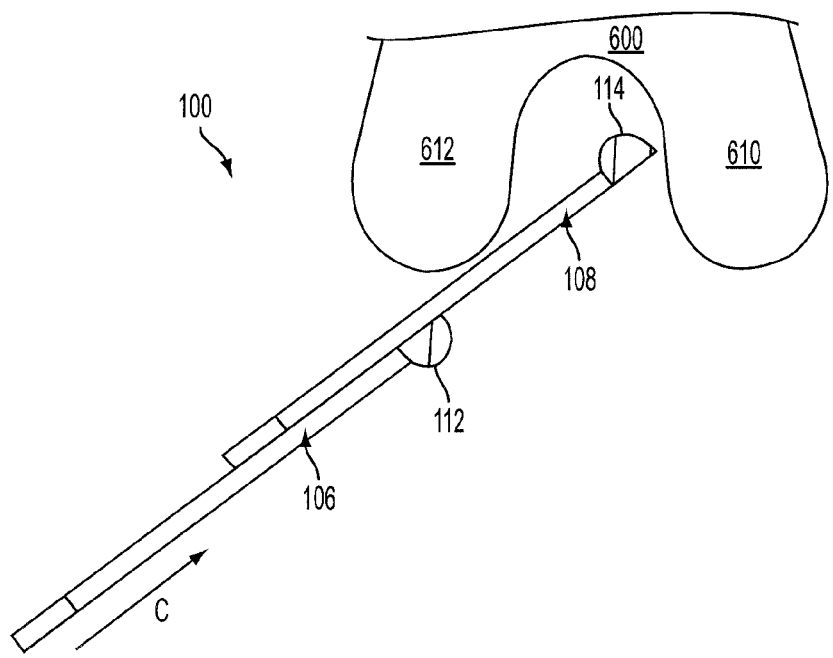
FIG. 16 is a side view of the bone reamer and femur of FIG. 15 with the bone reamer in a retracted configuration and rotated approximately 180 degrees about a longitudinal axis of the bone reamer relative to the position of the bone reamer in FIG. 14.

With reamer 100 positioned in the retracted position and the second cutting element 114 positioned adjacent to a bone surface of the lateral condoyle 610, the reamer 100 can be rotated approximately 180 degrees, for example, in the direction shown by arrow "B" in FIG. 15, to position the first elongate shaft 106 and first cutting element 112 away from the articulating surface of the medial condoyle 612, as shown in FIG. 16. With the first cutting element 112 safely positioned away from the surface of medial condoyle 612, the first elongate shaft 106 can be slid in a distal direction relative to second elongate shaft 108, in the direction shown by arrow "C," to move the reamer 100 from the retracted configuration to the non-retracted configuration.

Figure 17:
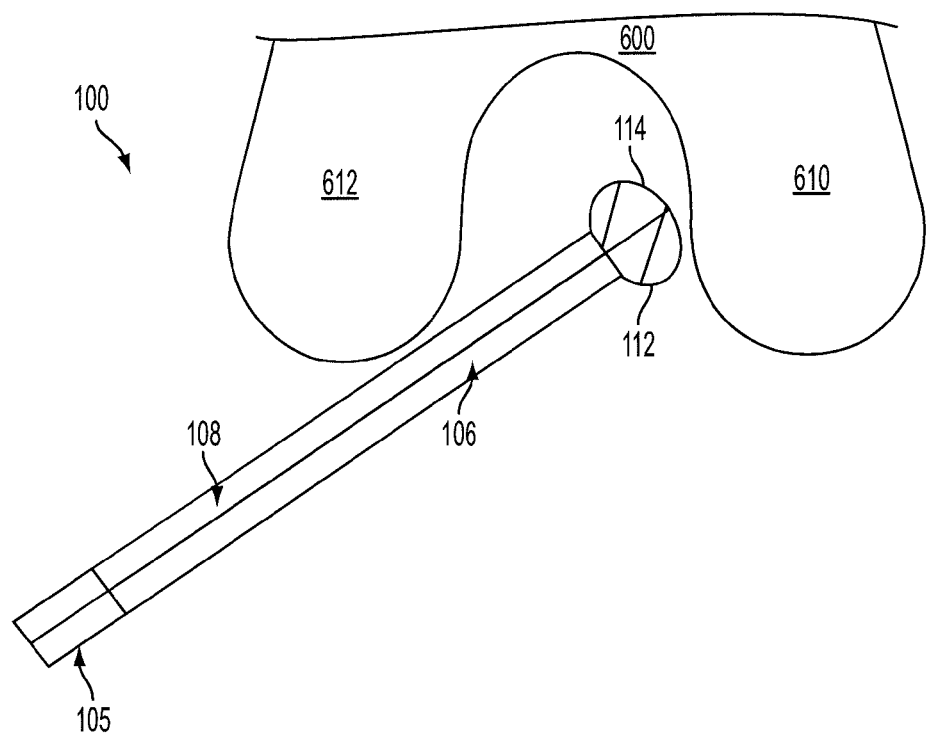
FIG. 17 is a side view of the bone reamer and femur of FIG. 16 with the bone reamer in a non-retracted configuration and positioned adjacent to the lateral condoyle of the femur.

FIG. 17 illustrates the reamer 100 in the non-retracted position with the first and second cutting elements 112, 114 positioned adjacent to one another to form the unitary cutting element 104. In embodiments that include the locking features described above, locking features can be employed to ensure the first and second shafts 106, 108 are fully in the non-retracted position, and to maintain the reamer 100 in the non-retracted position during subsequent drilling. With the reamer 100 in the non-retracted position, and positioned adjacent to the desired entry point of a femoral tunnel, a proximal portion of reamer 100 can be coupled to a driver 500 (not shown) by any of the devices described herein, and the reamer 100 can be used to drill a femoral tunnel according to methods well known in the art. When drilling of the femoral tunnel is complete, the reamer 100 can be removed from the patient through the AM portal by following, in reverse order, the steps of the method for inserting the reamer 100 through the AM portal described above.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A method for forming a bore hole in bone, comprising:
    inserting a distal portion of a bone reamer through tissue to position the distal portion of the bone reamer adjacent to bone, the bone reamer comprising a first portion of a shaft longitudinally slidably coupled to a second portion of the shaft, a first cutting element disposed on a distal end of the first portion of the shaft, and a second cutting element disposed on a distal end of the second portion of the shaft;
    slidably advancing one of the first and second portions of the shaft relative to one another to position the first and second cutting elements a distance apart from one another;
    rotating the first portion of the shaft of the bone reamer and the first cutting element;
    slidably advancing one of the first and second portions of the shaft relative to one another to position the first and second cutting elements adjacent to one another; and
    activating a driver coupled to the bone reamer to rotate the bone reamer and thereby cause the first and second cutting elements to form a bore hole in the bone.

2. The method of claim 1, wherein rotating the first portion of the shaft of the bone reamer rotates the second cutting element such that the second cutting element is positioned away from a medial condyle.

3. The method of claim 1, wherein the first and second cutting elements are positioned adjacent to one another when the bone reamer is inserted through tissue.

4. The method of claim 1, wherein inserting the bone reamer through tissue comprises positioning the distal end of the bone reamer adjacent to a medial condyle of a femur.

5. The method of claim 1, wherein the bone reamer is advanced over a guidewire.

* * * * *